United States Patent [19]
Simon et al.

[11] Patent Number: 5,891,146
[45] Date of Patent: Apr. 6, 1999

[54] WEDGE ORTHOPEDIC SCREW

[75] Inventors: Timothy M. Simon, Los Alamitos, Calif.; Harold M. Aberman, Montclair, N.J.

[73] Assignee: Applied Biological Concepts, Inc., Los Alamitos, Calif.

[21] Appl. No.: 953,856

[22] Filed: Oct. 15, 1997

[51] Int. Cl.$^6$ ................................................. A61B 17/58
[52] U.S. Cl. ..................... 606/71; 606/76; 411/414; 411/426
[58] Field of Search .................. 606/60, 72, 73, 606/65; 623/13; 411/411, 414, 415, 424, 426

[56] References Cited

U.S. PATENT DOCUMENTS

| | | | |
|---|---|---|---|
| 4,854,311 | 8/1989 | Steffee | 606/66 |
| 5,169,400 | 12/1992 | Muhling et al. | 606/73 |
| 5,364,400 | 11/1994 | Rego, Jr. et al. | 606/72 |
| 5,425,407 | 6/1995 | Archuleta et al. | 152/370 |
| 5,443,509 | 8/1995 | Boucher et al. | 623/16 |
| 5,456,685 | 10/1995 | Huebner | 606/73 |
| 5,571,139 | 11/1996 | Jenkins, Jr. | 606/232 |

*Primary Examiner*—Michael Buiz
*Assistant Examiner*—David O. Reip
*Attorney, Agent, or Firm*—Fulwider Patton Lee & Utecht, LLP

[57] ABSTRACT

An orthopedic interference screw for compression anchoring a bone graft in a bore formed in a bone mass. The interference screw includes a biocompatible body with a root. A screw thread is formed over substantially all of the root. The screw thread includes buttress structure on only one side of the screw thread so that forces applied to the screw thread from a side remote from the buttress structure will be buttressed by the buttress structure.

18 Claims, 12 Drawing Sheets

WEDGE ORTHOPEDIC SCREW

FIELD OF THE INVENTION

This invention relates to an orthopedic interference screw for compression anchoring a bone graft in a bore formed in a bone mass and a method of endosteal fixation of the respective ends of the graft in the bore using differently structured screws at the respective ends.

BACKGROUND OF THE INVENTION

The anterior cruciate ligament (ACL) is frequently injured in contact sports and other activities. Such injuries cause instability in the knee to an extent that ACL reconstruction may be required. Medical procedures have developed over the years to enable in ACL reconstruction, the substitution of a ligament or graft and attaching both ends thereof to the distal femur or proximal tibia to facilitate regrowth and permanent attachment. One method for increasing the strength of the graft attachment comprises wedging an interference screw between a graft bone block and an interior wall of a bore (osseous tunnel) formed through the bone mass. Tension forces applied to the graft after it has been attached to the femur and tibia are considerable and it is essential that the interference screw so utilized in the medical procedure have sufficient strength to resist the tendencies for the replacement ligament (graft) to pull out of the osseous tunnels formed in the bone mass.

Applicants have noted that the tendency for interference screws to pull out of the osseous tunnels when considerable forces are applied to the substitute ligament are caused in part by either weak bone structure or flexure of the thread design utilized on the interference screws. Thus, a need remains for a high strength interference screw for use in surgical procedures, such as ACL reconstruction.

Accordingly, it is an object of this invention to provide an orthopedic interference screw for compression anchoring a bone graft in an osseous tunnel formed in a bone mass.

It is a further object of the invention to provide an orthopedic interference screw for use in ACL reconstruction.

It is a further object of the invention to provide an orthopedic interference screw, as aforesaid, which is made of a biocompatible material and having a root with front and back ends and further including an outer surface with a uniform taper at a root taper angle to a longitudinal axis of the screw and the formation of a screw thread over substantially all of the root, the screw thread including crests with a uniform surface area along the length thereof and uniformly spirally expanding from the outer surface of the root over at least the front end of the screw so that an aggregate of the crests form at least at the aforesaid front end of the screw a crest taper angle greater than the root taper angle.

It is a further object of the invention to provide an orthopedic interference screw, as aforesaid, wherein the root has front and back ends and further includes an outer surface with a uniform taper at a root taper angle to a longitudinal axis of the screw between the front and back ends, wherein a screw thread is formed over substantially all of the root, the screw thread including crests with a uniform surface area along a length thereof and uniformly spirally expanding from the outer surface of the root from the front end to the back end so that an aggregate of the crests form a crest taper angle greater than the root taper angle, and wherein the screw thread includes a buttress construction on only one side of the screw thread capable of reinforcing the screw thread so that forces applied to a graft bone block engaged with the screw thread will be buttressed by the aforesaid buttress construction forming a part of the screw thread construction.

It is a further object of the invention to provide both non-cannulated and cannulated versions of the inventive screws, as aforesaid.

It is a further object of the invention to provide an orthopedic interference screw, as aforesaid, which can be utilized in a medical procedure for endosteal fixation of a graft including the method step of selecting at least two different screws, one screw having buttressed threads oriented on an axially facing side facing toward the tip end of the screw and the other screw having buttress threads thereon which are each oriented on an axially facing side facing toward a head end of the screw.

It is a further object of the invention to provide a method of endosteal fixation, as aforesaid, wherein each of the screws is cannulated to facilitate installation of the respective screws utilizing a guide wire positioned through the osseous tunnel and each of the respective screws during the screw installation process.

SUMMARY OF THE INVENTION

The objects and purposes of the invention are met by providing an orthopedic interference screw for compression anchoring a bone graft in a bore formed in a bone mass. The interference screw includes a biocompatible body with a root. A screw thread is formed over substantially all of said root. The screw thread includes buttress means on only one side of said screw thread so that forces applied to the screw thread from a side remote from said buttress means will be buttressed by said buttress means.

The objects and purposes of the invention are further met by providing a method of endosteal fixation and a method of endosteal fixation of the respective ends of the graft in the bore using differently structured screws at the respective ends.

BRIEF DESCRIPTION OF THE DRAWINGS

Other objects and purposes of this invention will be apparent to persons acquainted with screws of this general type and with associated medical procedures upon reading the following specification and inspecting the accompanying drawings, in which.

3

DETAILED DESCRIPTION

FIGS. 1 to 5 illustrate a first embodiment of an orthopedic interference screw 10 embodying our invention. The screw 10 has a biocompatible body $B_1$ with an elongated root portion 11 with a circular cross-sectional shape. The root portion 11 includes a front or tip end 12 and a back or head end 13. A thread 14 is formed over substantially the entire root section 11 from the tip end 12 to the back end 13.

In this particular embodiment, the root portion 11 is, as stated above, circular in cross section and is uniformly tapered at a root taper angle $\theta_1$ that is in the range of 5.8° to 6.2°. The screw thread 14 formed over substantially all of the root includes crests 16 with a uniformly wide at width $W_1$ surface area along a length thereof and uniformly spirals expanding from the outer surface of the root from the tip end to the back end so that an aggregate of the crests 16 form a crest taper angle $\Phi_1$ greater than the root taper angle $\theta_1$. In this particular embodiment, the crest taper angle is in the range of 10.6° to 11.6°. In a preferred embodiment, the root taper angle $\theta_1$ is 6° and the crest taper angle $\Phi_1$ is 11°.

Figures 5, 6, 7, 8, 9, 10:
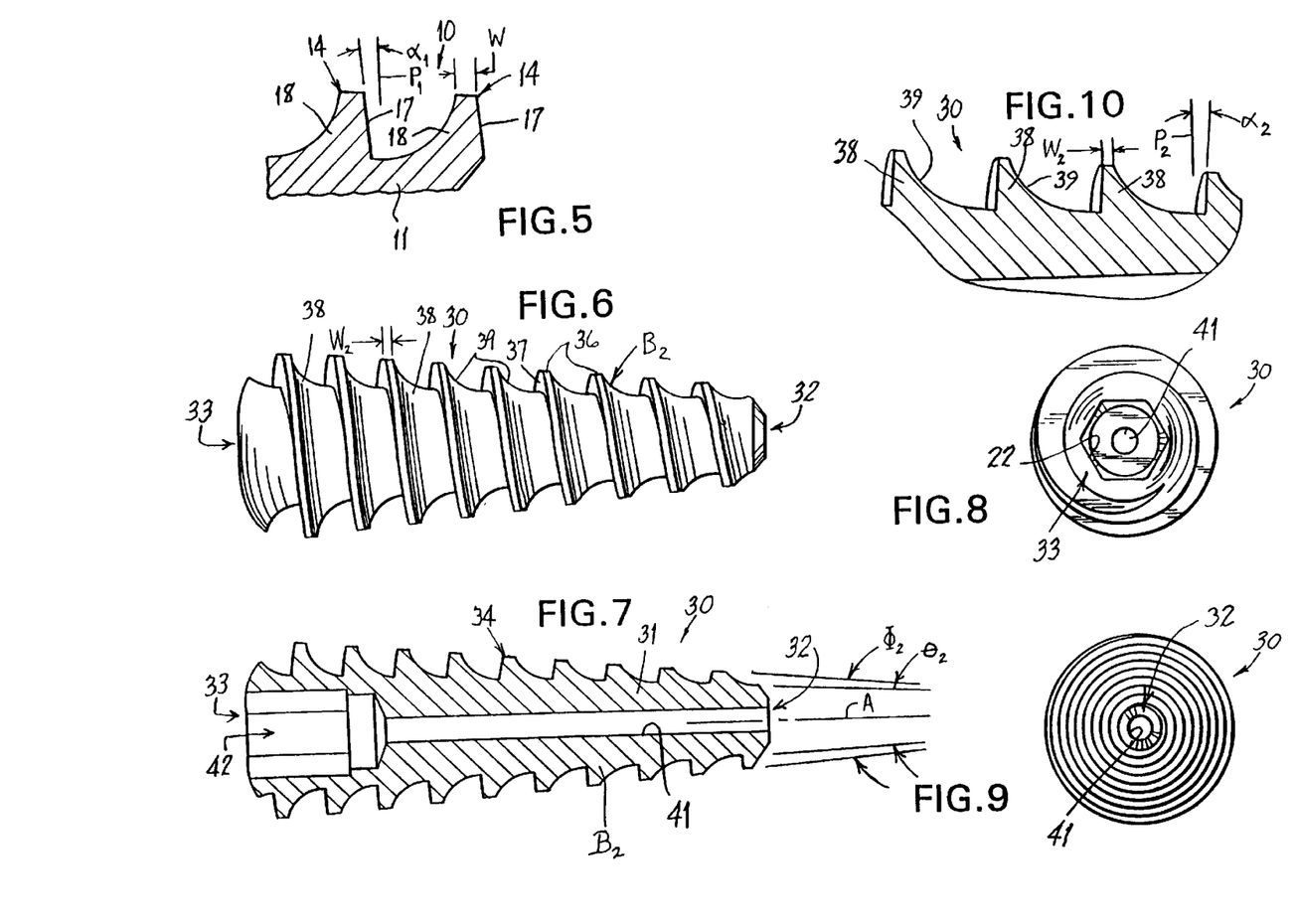
FIG. 5 is an enlarged sectional view of the thread on the screw illustrated in FIG. 1.
FIG. 6 is a second embodiment of an interference screw embodying our invention.
FIG. 7 is a central longitudinal sectional view of the screw illustrated in FIG. 6.
FIG. 8 is a left end view of FIG. 6.
FIG. 9 is a right end view of FIG. 6.
FIG. 10 is an enlarged sectional view of the thread illustrated on the screw of FIG. 6.

The axially facing side 17 of the screw thread 14 facing the tip end 12 is inclined toward the back end and to a plane $P_1$ perpendicular to the longitudinal axis A at an angle $\alpha_1$ which, in this particular embodiment, is generally 5°. The side of the screw thread remote from the surface 17 includes a buttress 18. The axially facing surface of the buttress 18 is concavely radiused as at 19.

Figure 1:
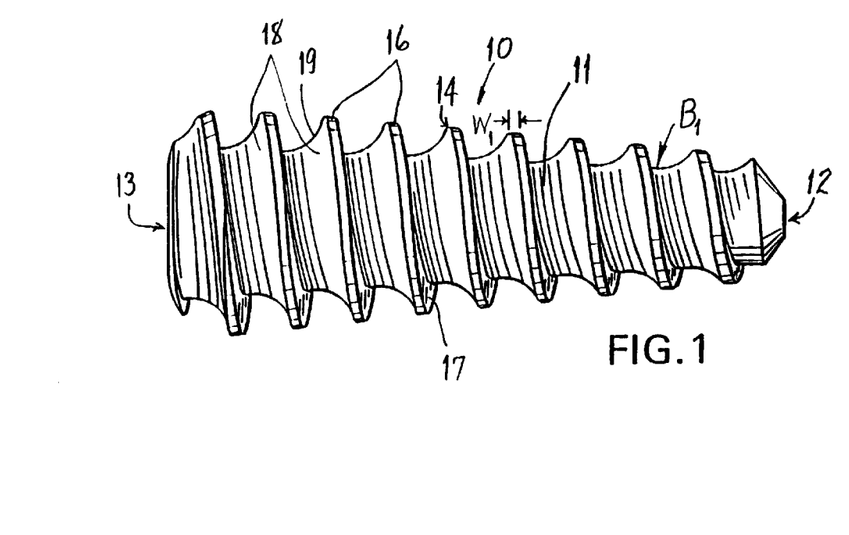
FIG. 1 is a front view of a first embodiment of the interference screw embodying our invention.
Figure 2:
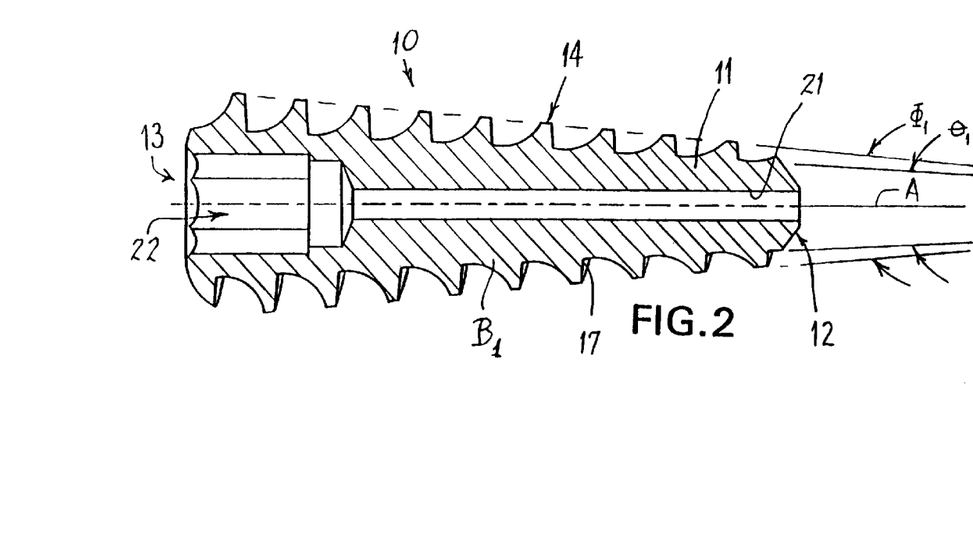
FIG. 2 is a longitudinal sectional view of the screw illustrated in FIG. 1.
Figure 3:
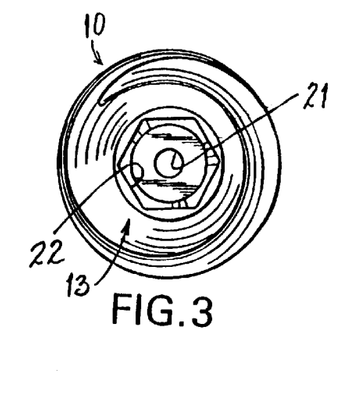
FIG. 3 is a left end view thereof.
Figure 4:
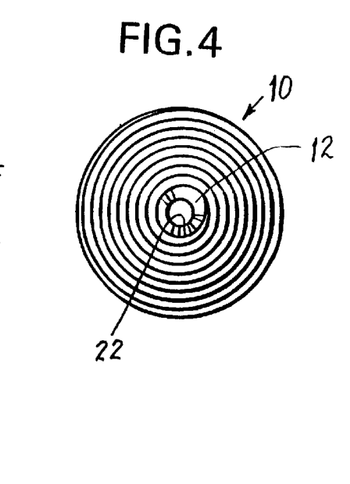
FIG. 4 is a right end view thereof.

As is illustrated in FIG. 2, the screw 10 is uniformly cannulated as at 21. However, a not shown non cannulated version of the screw is within the scope of the invention. In the cannulated embodiment, the cannulation extends from the tip end 12 to a hexagonally shaped socket 22 formed in the head end 13 and opening outwardly axially of the head end 13 as illustrated in FIG. 2. The hexagonally-shaped socket 22 has a depth sufficient to receive therein a complementarily-shaped driving instrument for effecting a rotative driving of the screw 10. The cannulation 21 also is adapted to receive therein a guide wire schematically illustrated in FIG. 32. In this particular embodiment, the biocompatible body is made of a biocompatible metal, or a nonabsorbable polymer or a bio-absorbable material or a ceramic material or a bioceramic material, any one of which can also be coated with a bio-absorbable coating having a low coefficient of friction. The coating can consist of pharmaceuticals and bone growth factors.

FIGS. 6–10 illustrate a second embodiment of an orthopedic interference screw 30 embodying our invention. The screw 30 has a biocompatible body $B_2$ with an elongated root portion 31 with a circular cross-sectional shape. The root portion 31 includes a front or tip end 32 and a back or head end 33. A thread 34 is formed over substantially the entire root section 31 from the tip end 32 to the back end 33. In this particular embodiment, the root portion 31, as stated above, is circular in cross section and is uniformly tapered at a root taper angle $\theta_2$ that is in the range of 5.8° to 6.2°. The screw thread 34 formed over substantially all of the root includes crests 36 with a uniformly wide at width $W_2$ surface area along a length thereof and uniformly spirals expanding from the outer surface of the root from the tip end 32 to the back end 33 so that an aggregate of the crests 36 form a crest taper angle $\Phi_2$ greater than the root taper angle $\theta_2$. In this particular embodiment, the crest taper angle is in the range of 10.6° to 11.6°. In a preferred embodiment, the root taper angle $\theta_2$ is 6° and the crest taper angle $\Phi_2$ is 11.4°.

The axially facing side 37 of the screw thread 34 facing the head end 33 is inclined toward the tip end and to a plane $P_2$ perpendicular to the longitudinal axis A at an angle $\alpha_2$ which, in this particular embodiment, is generally 5°. The side of the screw thread remote from the surface 37 includes a buttress 38. The axially facing surface of the buttress 38 is concavely radiused as at 39.

As is illustrated in FIG. 7, the screw 30 is uniformly cannulated as at 41. However, a not shown non cannulated version of the screw is within the scope of the invention. In the cannulated embodiment, the cannulation extends from the tip end 32 to a hexagonally shaped socket 42 formed in the head end 33 and opening outwardly axially of the head end 33 as illustrated in FIG. 7. The hexagonally-shaped socket 42 has a depth sufficient to receive therein a complementarily-shaped driving instrument 56 (FIG. 32) for effecting a rotative driving of the screw 30. The cannulation 41 is also adapted to receive therein a guide wire 54 schematically illustrated also in FIG. 32.

The materials of the second embodiment of our screw are the same as has been disclosed above with respect to the first embodiment.

Figure 33:
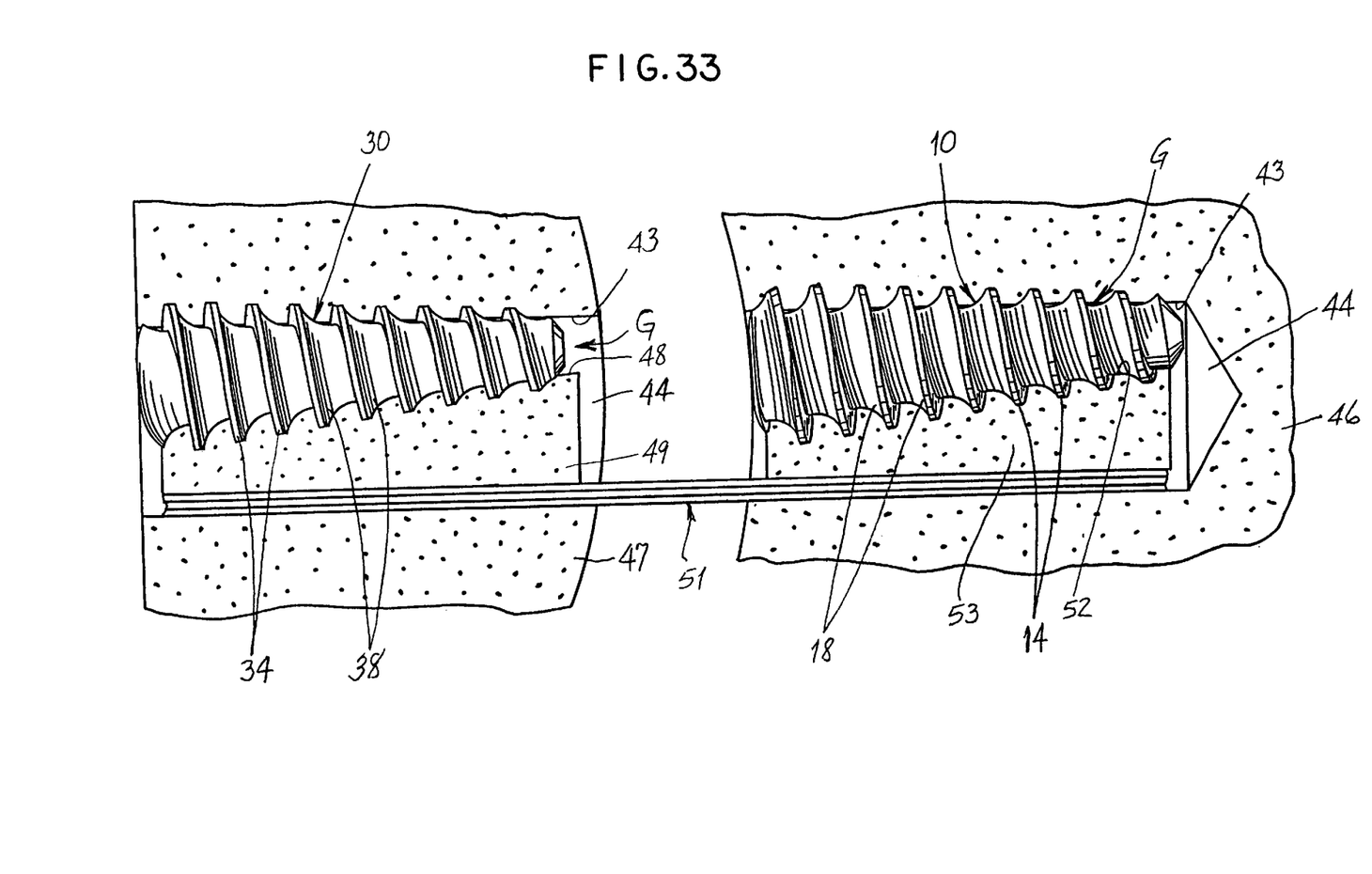
FIG. 33 is a highly schematic illustration of the tibia and femur with a substitute ligament extending therebetween and interference screws embodying our invention locking the substitute ligament to the bone mass.

It will be noted that the first embodiment screw 10 and the second embodiment screw 30 are similarly related except that the buttresses 18 and 38 are, respectively, on opposite sides of the respective threads 14 and 34. Referring to FIG. 33, it will be noted that the screws 10 and 30 are schematically illustrated as having been inserted into the respective gaps G between the internal wall 43 of an osseous tunnel 44 provided in the femur 46 and tibia 47 and the opposing surface 48 of a bone block 49 at one end of a substitute graft 51 and the opposing surface 52 of the bone block 53 at the other end of the substitute graft 51. It will be noted that once the screws have been correctly positioned in the gaps, a sufficient compressing of the ends of the graft 51 between the screws and the walls 43 of the respective osseous tunnels will have occurred. Thereafter, if the substitute graft 51 is subjected to tension, the oppositely oriented buttresses 18 and 38 will strengthen the respective threads 14 and 34 so as to prevent the respective bone blocks 49 and 53 from pulling out of the respective osseous tunnels 43 in the tibia 47 and the femur 46.

The tapered form of the screws 10 and 30 facilitate an insertion thereof into the respective gaps G with a uniform turning force which remains fairly constant as the screw is inserted into the respective gaps G until the compression force begins to develop. In this particular embodiment, the bone blocks 49 and 53 have surfaces 48 and 52 which are also tapered so as to optimize the threaded engagement thereof with the respective threads 14 and 34 of the respective screws 10 and 30 before the development of sufficient compression forces occurs.

The screws 10 and 30 can also be used with substitute grafts having cylindrically-shaped bone blocks instead of the trapezoidally-shaped bone blocks illustrated in FIG. 33.

Figure 32:
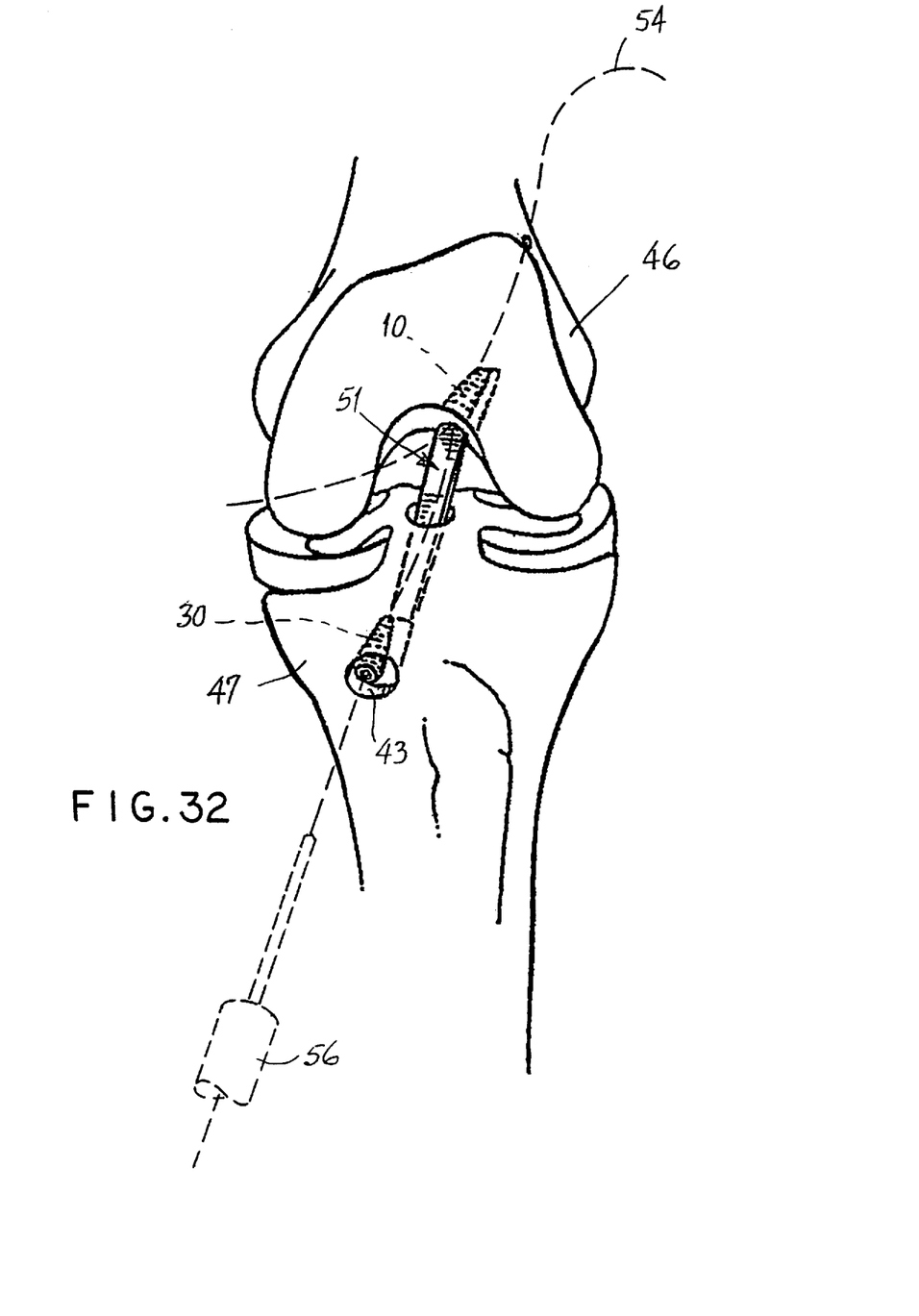
FIG. 32 is a view similar to FIG. 31, except that a guide wire is shown for assisting in the installation of the respective interference screws.

It will become important for the surgeon to become familiar with the use of two differing interference screws in practicing, for example, ACL reconstruction and effecting a compression anchoring of the bone graft 51 in the osseous tunnels formed in the femur and the tibia. In addition, and in view of the past use of a guide wire 54 with other known cannulated screws, it will be a familiar practice for the surgeon to use a guide wire 54 such as is schematically illustrated in FIG. 32 in facilitating an insertion of the screw into the respective femur and tibia utilizing a tool 56 having a hex-shaped driving end thereon which is receivable into the respective hex-shaped socket 22 and 42.

Figure 11:
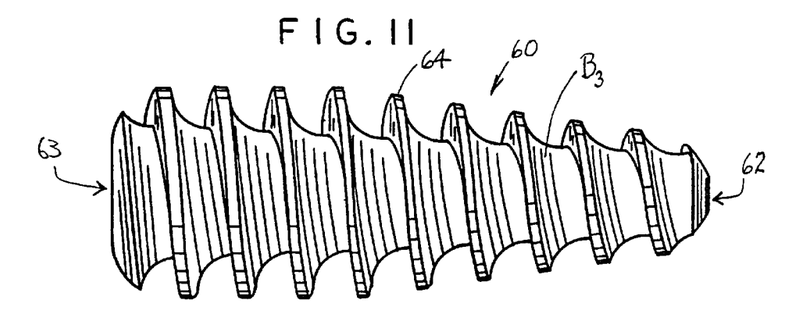
FIG. 11 is a third embodiment of an interference screw embodying our invention.
Figure 12:
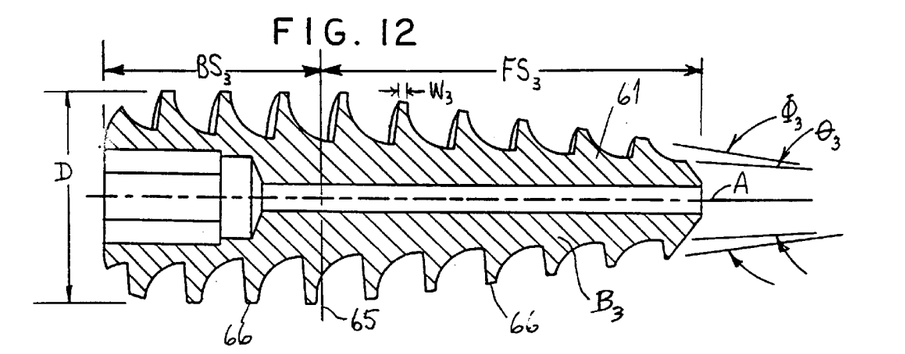
FIG. 12 is a central longitudinal sectional view of FIG. 11.
Figure 13:
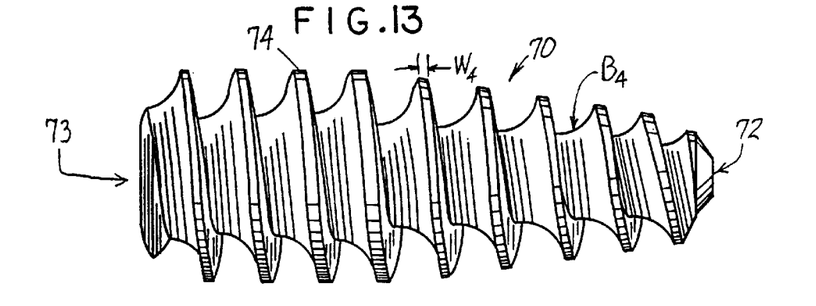
FIG. 13 is a fourth embodiment of an interference screw embodying our invention.
Figure 14:
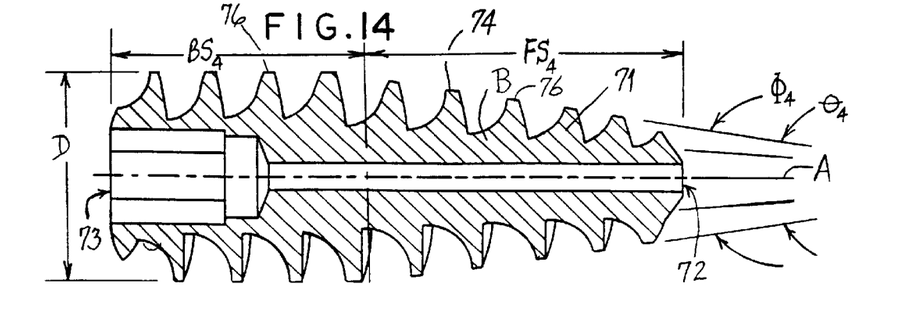
FIG. 14 is a central longitudinal sectional view of FIG. 13.
Figure 15:
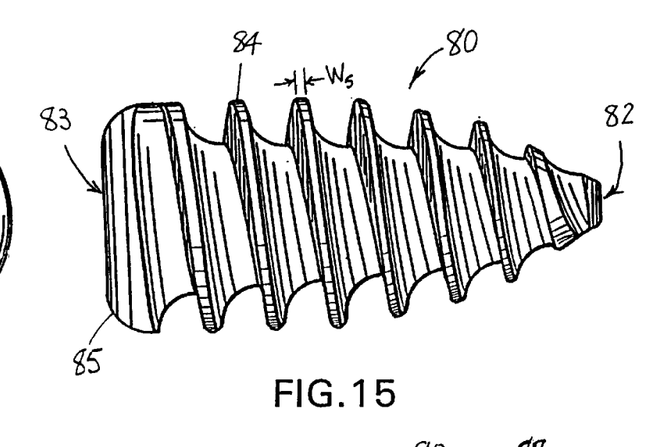
FIG. 15 is a fifth embodiment of an interference screw embodying our invention.
Figure 16:
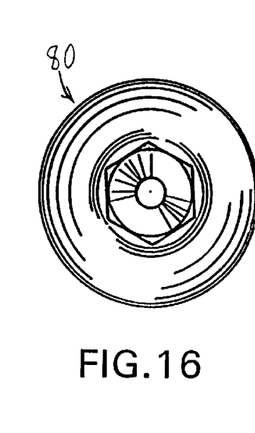
FIG. 16 is a left end view of FIG. 15.
Figure 17:
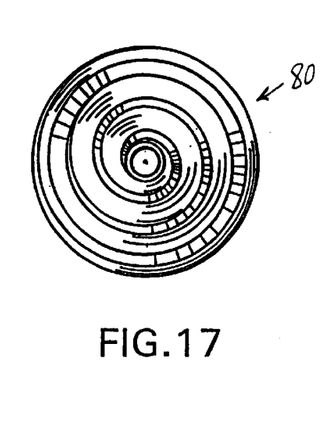
FIG. 17 is a right end view of FIG. 15.
Figure 18:
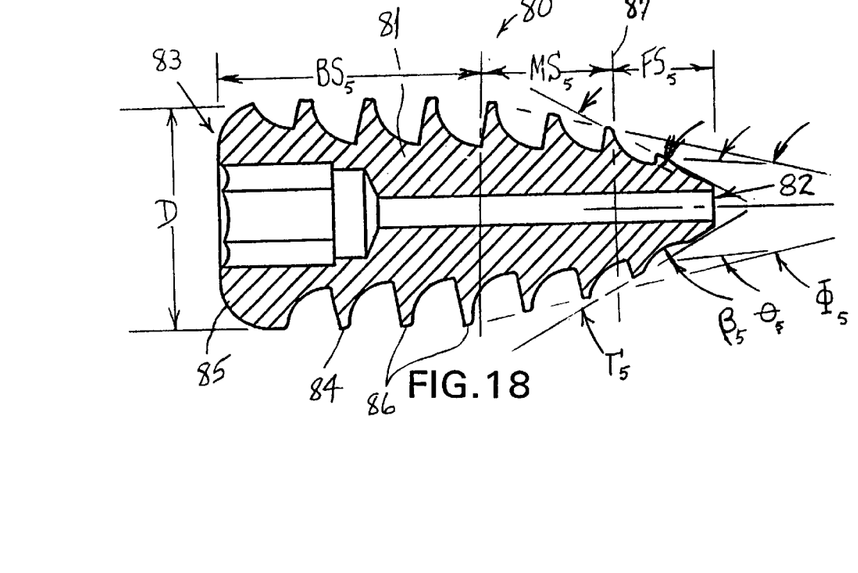
FIG. 18 is a central longitudinal sectional view of FIG. 15.
Figure 19:
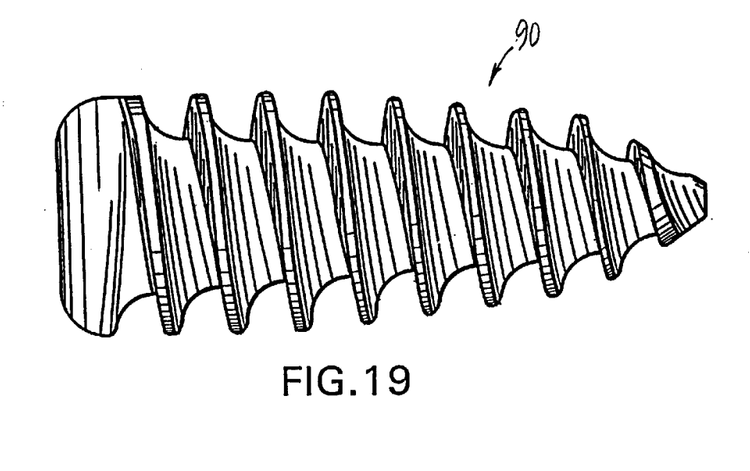
FIG. 19 is a sixth embodiment of an interference screw embodying our invention.
Figure 20:
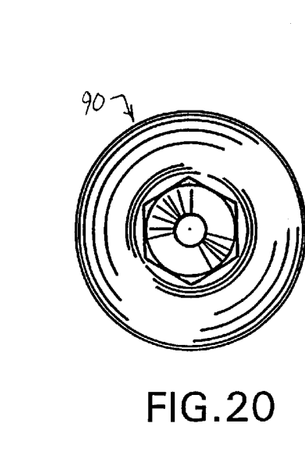
FIG. 20 is a left end view of FIG. 19.
Figure 21:
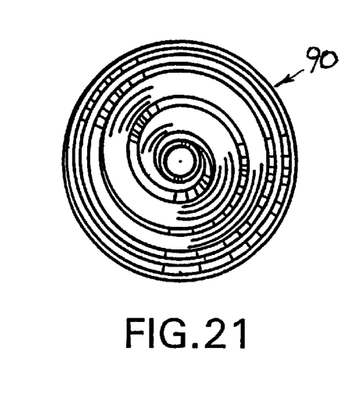
FIG. 21 is a right end view of FIG. 19.
Figure 22:
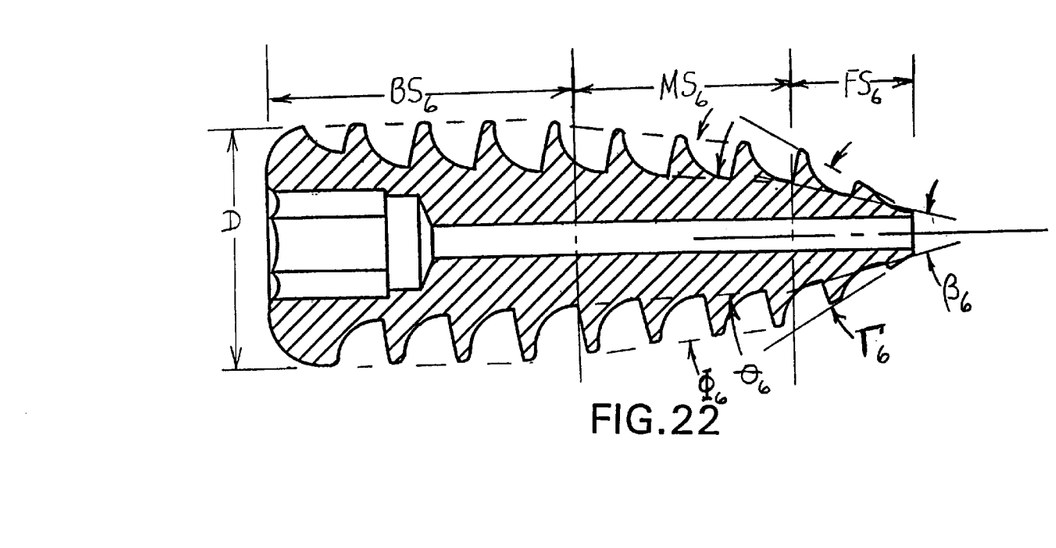
FIG. 22 is a central longitudinal sectional view of FIG. 19.
Figure 23:
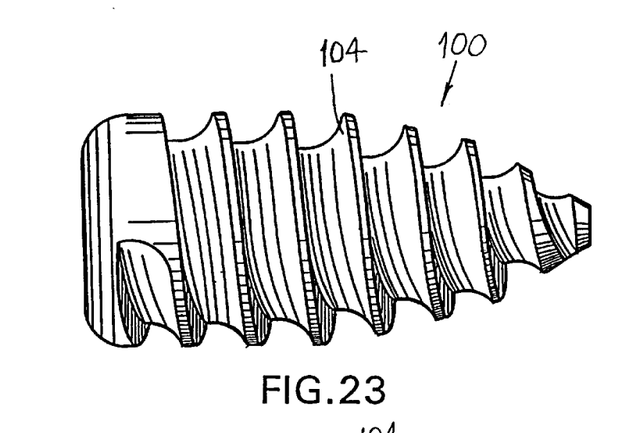
FIG. 23 is a seventh embodiment of an interference screw embodying our invention.
Figure 24:
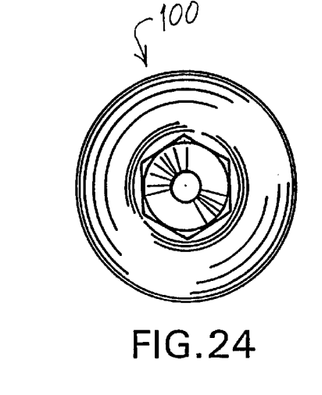
FIG. 24 is a left end view of FIG. 23.
Figure 25:
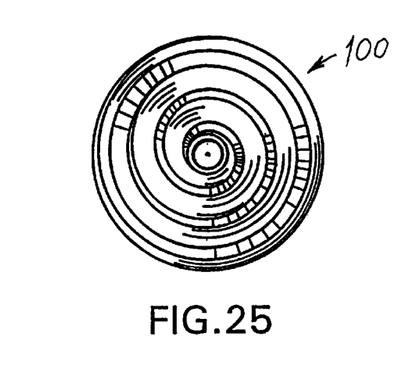
FIG. 25 is a right end view of FIG. 23.
Figure 26:
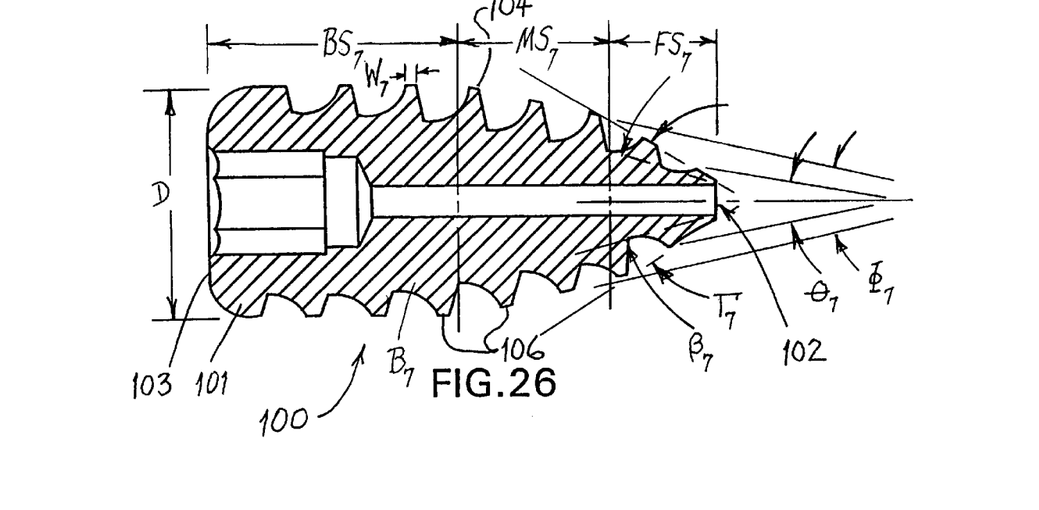
FIG. 26 is a central longitudinal sectional view of FIG. 23.
Figure 27:
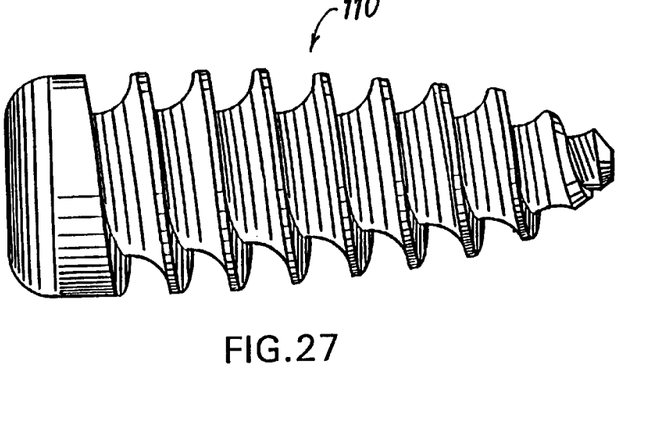
FIG. 27 is an eighth embodiment of an interference screw embodying our invention.
Figure 28:
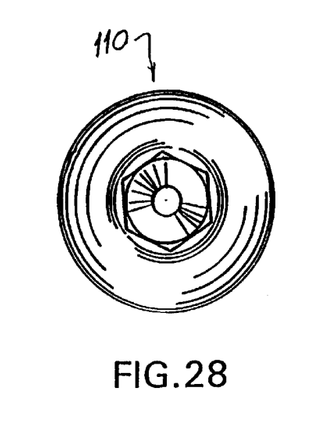
FIG. 28 is a left end view of FIG. 27.
Figure 29:
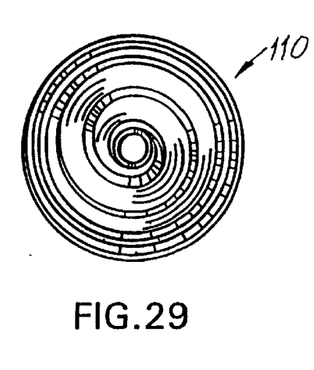
FIG. 29 is a right end view of FIG. 27.
Figure 30:
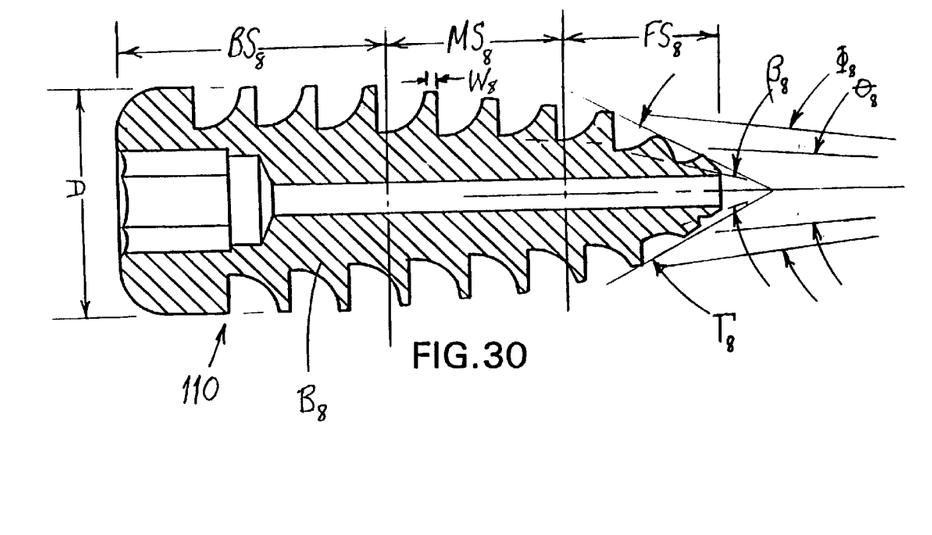
FIG. 30 is a central longitudinal sectional view of FIG. 27.
Figure 31:
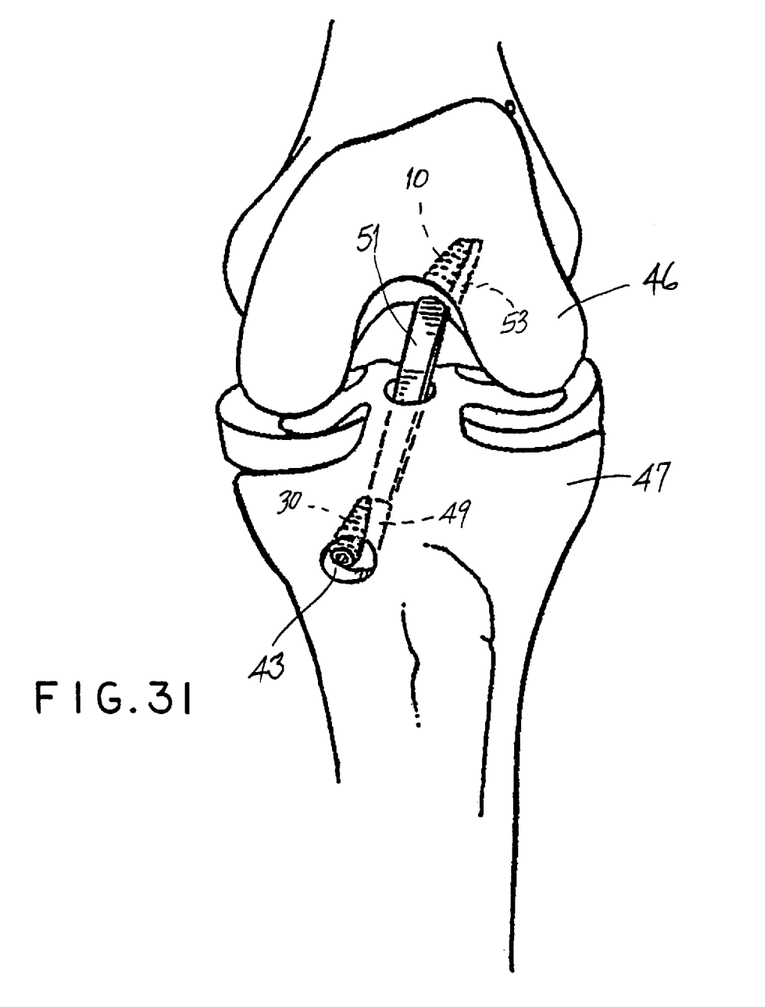
FIG. 31 is an isometric view of the femur and tibia with a substitute ligament fixedly oriented therebetween.

The third embodiment of FIGS. 11 and 12 and the fourth embodiment of FIGS. 13 and 14 are mere extensions of the technology set forth respectively in the second embodiment of FIGS. 6–10 and the first embodiment of FIGS. 1–5. More specifically, the orthopedic interference screw 60 of the third embodiment includes a cannulated or a non-cannulated biocompatible body $B_3$ with an elongated root portion 61 with a circular cross-sectional shape. The root portion 61 includes a front or tip end 62 and a back or head end 63. A thread 64 is formed over substantially the entire root section 61 from the tip end 62 to the back end 63.

In this particular embodiment, the root portion 61 is uniformly tapered at a root taper angle $\theta_3$ over the entire length of a front section $FS_3$, the root taper angle $\theta_3$ being in the range of 5.8° to 6.2°. The back section $BS_3$ of the root 61 of the screw 60 has a generally cylindrical form. The screw thread 64 formed over substantially all of the root 61 includes crests 66 with a uniformly wide at width $W_3$ surface area along a length thereof and uniformly spirals expanding from the outer surface of the root from the tip end 62 to a juncture 65 between the front section $FS_3$ and the back section $BS_3$ and thereafter extends in a cylindrical form at a diameter D to the back end. An aggregate of the crests 66 in the front section $FS_3$ form a crest taper angle $\Phi_3$ greater than the root taper angle $\theta_3$ and a cylinder throughout the length of the back section $BS_3$. In this particular embodiment, as with the embodiment of FIGS. 6–10, the crest taper angle is in the range of 10.6° to 11.6°. In a preferred embodiment, the root taper angle $\theta_3$ in the front section $FS_3$ is 6° and the crest taper angle $\Phi_3$ is 11°. All other characteristics of the interference screw 60 are the same as has been disclosed above with respect to the second embodiment.

The orthopedic interference screw 70 of the fourth embodiment shown in FIGS. 13 and 14 includes a cannulated or a non-cannulated biocompatible body $B_4$ with an elongated root portion 71 with a circular cross sectional shape. The root portion 71 includes a front or tip end 72 and a back or head end 73. A thread 74 is formed over substantially the entire root section 71 from the tip end 72 to the back end 73.

In this particular embodiment, the root portion 71 is uniformly tapered at a root taper angle $\theta_4$ over the entire length of a front section $FS_4$, the root taper angle $\theta_4$ being in the range of 5.8° to 6.2°. The back section $BS_4$ of the screw 70 has a generally cylindrical form. The screw thread 74 formed over substantially all of the root includes a crest 76 with a uniformly wide at width $W_4$ surface area along a length thereof and uniformly spirals expanding from the outer surface of the root from the tip end 72 to a juncture 75 between the front section $FS_4$ and the back section $BS_4$ and thereafter extends in a cylindrical form to the back end. An aggregate of the crests 76 form a crest taper angle $\Phi_4$ greater than the root taper angle $\theta_4$ in the front section $FS_4$ and a cylinder at a diameter D throughout the length of the back section $BS_4$. In this particular embodiment, as with the embodiment of FIGS. 1–5, the crest taper angle is in the range embodiment, the root taper angle $\theta_4$ in the front section $FS_4$ is 6° and the crest taper angle $\Phi_4$ is 11°. All other characteristics of the interference screw 70 are the same as has been disclosed above with respect to the first embodiment.

FIGS. 15–18 illustrate a fifth embodiment of an orthopedic interference screw 80 embodying our invention. The screw 80 has a cannulated or a non-cannulated biocompatible body B5 with an elongated root portion 81 with a circular cross-sectional shape. The root portion 81 includes three sections, namely, a front section $FS_5$, a midsection $MS_5$ and a back section $BS_5$. The root portion 81 also includes a front or tip end 82 and a back or head end 83. A thread 84 is formed over substantially the entire root section 81 from the tip end 82 to the back end 83.

In this particular embodiment, the front section $FS_5$ of the root portion 81 is uniformly tapered at a root taper angle $\beta_5$ that is in the range of 30° to 40°. The screw thread 84 includes crests 86 with a uniformly wide at width $W_5$ surface area along a length thereof in the front section $FS_5$ and uniformly spirals expanding from the outer surface of the root from the tip end 82 to a juncture 87 between the front section $FS_5$ and the mid-20 section $MS_5$ so that an aggregate of the crests 86 form a crest taper angle $\Gamma_5$ that is in the range of 55° to 65°. In this particular embodiment, the preferred crest taper angle $\Gamma_5$ in the front section $FS_5$ is 60° and the preferred root taper angle $\beta_5$ is in the range of 30° to 32°. The midsection $MS_5$ of the root portion 81 is uniformly tapered at a root taper angle $\theta_5$ that is in the range of 5.8° to 6.2°. The screw thread 84 formed over substantially all of the root forms a crest taper angle $\Phi_5$ greater than the root taper angle $\theta_5$. In this particular embodiment, the crest taper angle is, in the midsection $MS_5$, in the range of 17° to 26°. In a preferred embodiment, the root taper angle $\theta_5$ in the midsection $MS_5$ is 620 and the crest taper angle $\Phi_5$ in the midsection $MS_5$ is 19°.

The remaining characteristics of the screw, particularly the cylindrical features in the back section $BS_5$ are identical to the characteristics discussed above with respect to the third embodiment of FIGS. 11 and 12. There is, however, one exception and that is a rounded surface 85 has been provided at the back end 83. Other than this difference, the characteristics of the back section $BS_5$ are nearly the same as the characteristics of the back section $BS_3$ in the third embodiment of FIGS. 11 and 12. The angle $\alpha_5$ (not shown) is 8° in the preferred embodiment.

The sixth embodiment of FIGS. 19–22 is very similar to the fifth embodiment of FIGS. 15–18, except that the interference screw 90 of the sixth embodiment is longer than the screw 80 in the fifth embodiment. Another difference is that the midsection $MS_6$ in the sixth embodiment includes a root taper angle that is in the range of 5.8° to 6.2° and a crest taper angle that is in the range of 10.6° to 11.6°. In a preferred embodiment, the root taper angle $\theta_6$ in the midsection $MS_6$ is 6° and the crest taper angle $\Phi_6$ in the midsection $MS_6$ is 11°. Other than these differences, the characteristics of the screw 90 in the sixth embodiment is nearly the same as the characteristics of the screw in the fifth embodiment of FIGS. 15–18.

FIGS. 23–26 illustrate a seventh embodiment of an orthopedic interference screw 100 embodying our invention. The screw 100 has a cannulated or a non cannulated biocompatible body $B_7$ with an elongated root portion 101 with a circular cross-sectional shape. The root portion 101 includes three sections, namely, a front section $FS_7$, a midsection $MS_7$ and a back section $BS_7$. The root portion 101 also includes a front or tip end 102 and a back or head end 103. A thread 104 is formed over substantially the entire root section 101 from the tip end 102 to the back end 103.

In this particular embodiment, the front section $FS_7$ of the root portion 101 is uniformly tapered at a root taper angle $\beta_7$ that is in the range of 30° to 40°. The screw thread 104 includes crests 106 with a uniformly wide at width $W_7$ surface area along a length thereof in the front section $FS_7$ and uniformly spirals expanding from the outer surface of the root from the tip end to a juncture 107 between the front section $FS_7$ and the midsection $MS_7$. An aggregate of the crests 106 form a crest taper angle $\Gamma_7$ that is in the range of 55° to 65°. In this particular embodiment, the preferred crest taper angle $\Gamma_7$ in the front section $FS_7$ is 60° and the preferred root taper angle $\beta_7$ is in the range of 30° to 32°. The midsection $MS_7$ of the root portion 101 is uniform tapered at a root taper angle $\theta_7$ that is in the range of 5.8° to 6.2°. The screw thread 104 formed over substantially all of the root forms a crest taper angle $\Phi_7$ greater than the root taper angle $\theta_7$. In this particular embodiment, the crest taper angle is in the range of 18° to 26°. In a preferred embodiment, the root taper angle $\theta_7$ in the midsection $MS_7$ is 6° and the crest taper angle $\Phi_7$ in the midsection $MS_7$ is 19°. The remaining characteristics of the screw 100, particularly the features in the back section $BS_7$ are identical to the characteristics discussed above with respect to the fourth embodiment of FIGS. 13 and 14. There is, however, one exception and that is a rounded surface 105 has been provided at the back end 103. Other than this difference, the characteristics of the back section $BS_7$ are nearly the same as the characteristics of the back section $BS_4$ in the fourth embodiment of FIGS. 13 and 14.

The eighth embodiment of FIGS. 27–30 is very similar to the seventh embodiment of FIGS. 23–26, except that the interference screw 110 of the eighth embodiment is longer than the screw 100 in the seventh embodiment. Another difference is that the midsection $MS_8$ in the eighth embodiment includes a root taper angle that is in the range of 5.8° to 6.2° and a crest taper angle that is in the range of 10.6° to 11.6°. In a preferred embodiment, the root taper angle $\theta_8$ in the midsection $MS_8$ is 6° and the crest taper angle $\Phi_8$ in the midsection $MS_8$ is 11°. Other than these differences, the characteristics of the screw 110 in the eighth embodiment is nearly the same as the characteristics of the screw in the seventh embodiment of FIGS. 23–26.

Figure 34:
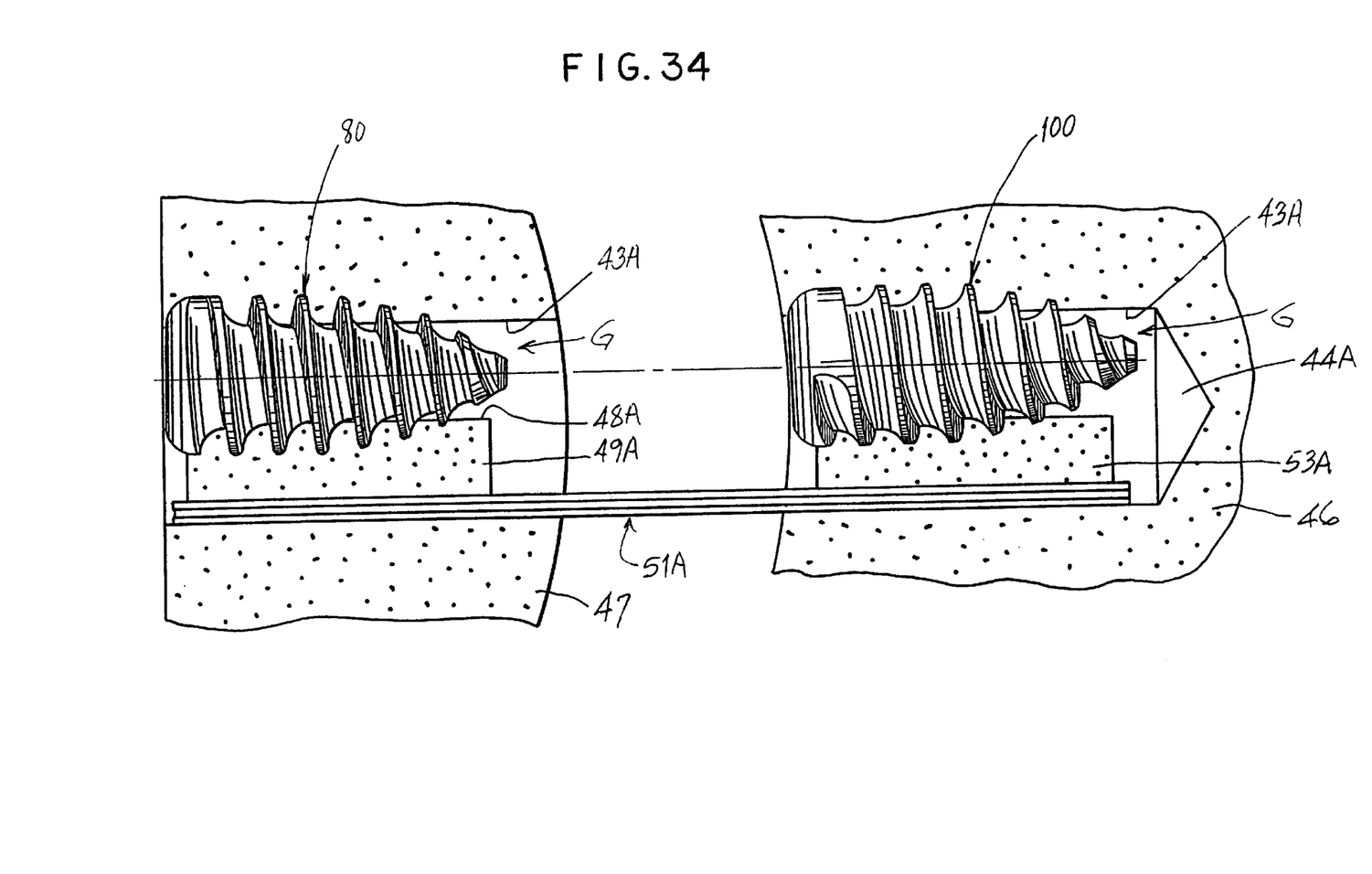
FIG. 34 is a highly schematic illustration of the tibia and femur with a substitute ligament extending therebetween and interference screws embodying our invention locking the substitute ligament to the bone mass.

It will be noted that the fifth and seventh embodiments and the sixth and eighth embodiments are each similarly related, except that the buttresses are, respectively, on opposite sides of the respective threads. Referring to FIG. 34, it will be noted that the screws 80 and 100 are schematically illustrated as having been inserted into the respective gaps G between the internal wall 43A of an osseous tunnel 44A provided in the femur 46 and tibia 47 and the opposing surface 48A of a bone block 49A at one end of a substitute graft 51A and the opposing surface 52A of the bone block 53A at the other end of the substitute graft 51A. It will be noted that once the screws 80 and 100 have been correctly positioned in the gaps, a sufficient compressing of the end of the graft 51 between the screws and the walls 43A of the respective osseous tunnels will have occurred. Thereafter, if the substitute graft 51A is subjected to tension, the oppositely oriented buttresses will strengthen the respective threads so as to prevent the respective bone blocks 49A and 53A from pulling out of the respective osseous tunnels 43A in the tibia 47 and the femur 46. The tapered form of the screws 80 and 100 facilitate an insertion thereof into the respective gaps G with a turning force increasing as the screw becomes more inserted into the respective gaps G. In this particular embodiment, the bone blocks 49A and 53A are cylindrical, namely, they have surfaces 48A and 52A which are parallel to the wall 43A of the osseous tunnels. The cylindrical threads in the back sections of each of the screws 80 and 100 serve to more fully anchor each screw into a respective bone block and into the wall of the bone mass so as to prevent each screw from being inadvertently pulled out as the tension forces on the substitute graft increase.

Figure 35:
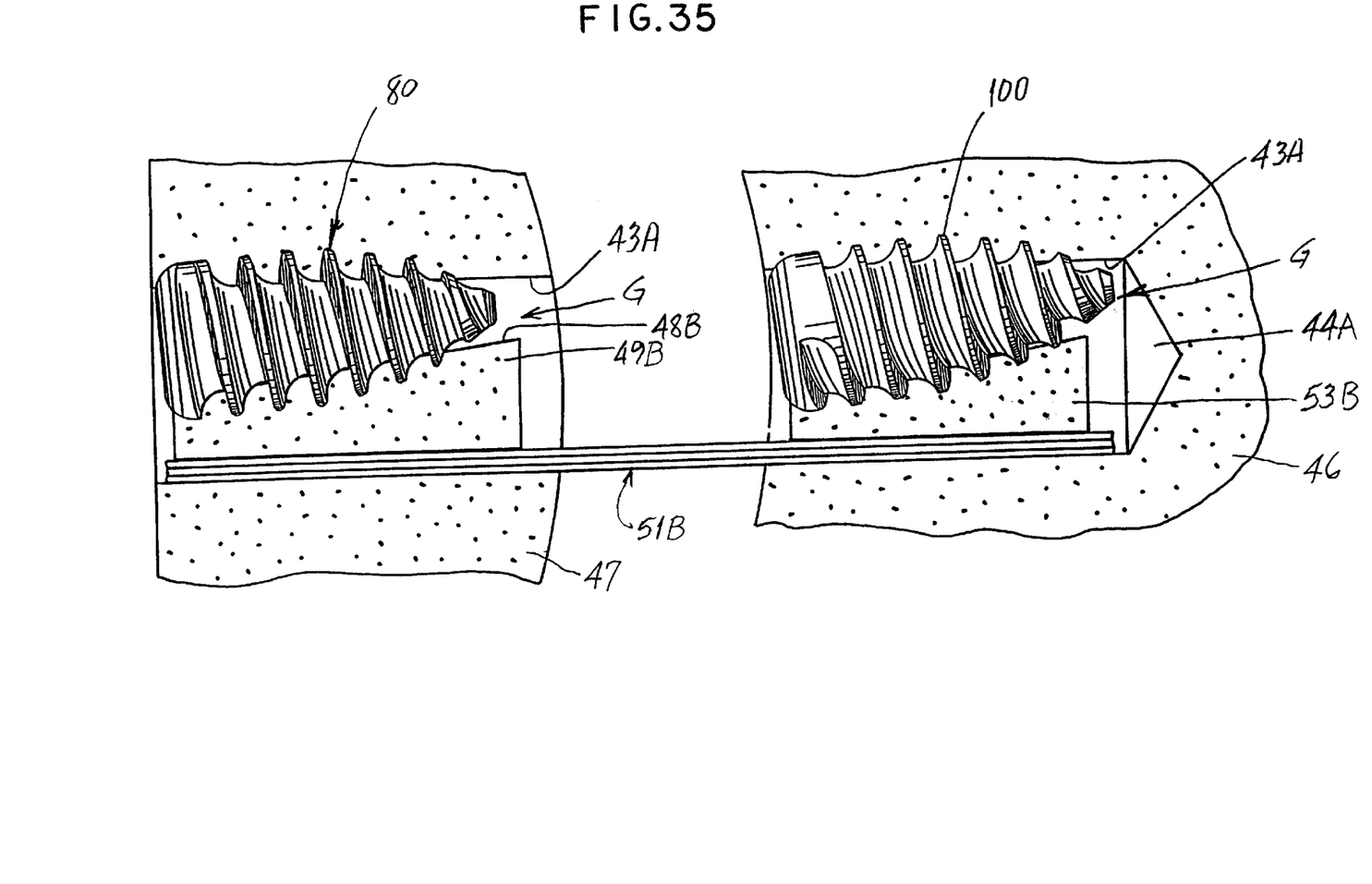
FIG. 35 is a highly schematic illustration of the tibia and femur with a substitute ligament extending therebetween and interference screws embodying our invention locking the substitute ligament to the bone mass.

The above analysis also applies to the screws illustrated in the sixth embodiment and the eighth embodiment. In addition, and as illustrated in FIG. 35, the same screws can be utilized with substitute grafts 51B having trapezoidally-shaped bone blocks 49B and 53B. The reference numbers used in FIG. 35 are the same as have been used in FIG. 34, but with the suffix "B" instead of the suffix "A". Thus, further discussion of FIG. 35 is believed unnecessary.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. An orthopedic interference screw for compression anchoring a bone graft in a bore formed in a bone mass, said screw comprising:

a biocompatible body with a root having front and back ends and further including an outer surface with a uniform taper at a root taper angle to a longitudinal axis of said screw between said front and back ends;

a screw thread formed over substantially all of said root, said screw thread including a crest with a uniform surface area along a length thereof and uniformly spirally expanding from said outer surface of said root from said front end to said back end so that an aggregate of said crests form a crest taper angle greater than said root taper angle.

2. The screw according to claim 1, wherein said screw thread includes buttress means on a side of said screw thread remote from said front end so that forces applied to said screw thread from said front end axially toward said back end will be buttressed by said buttress means.

3. The screw according to claim 1, wherein said screw thread includes buttress means on a side of said screw thread remote from said back end so that forces applied to said screw thread from said back end axially toward said front end will be buttressed by said buttress means.

4. The screw according to claim 1, wherein said screw is cannulated.

5. The screw according to claim 1, wherein said root taper angle is in the range of 5.8° to 6.2° and said crest taper angle is in the range of 10.6° to 11.6°.

6. The screw according to claim 5, wherein said screw thread includes buttress means on a side of said screw thread remote from said front end so that forces applied to said screw thread from said front end axially toward said back end will be buttressed by said buttress means.

7. The screw according to claim 6, wherein said root taper angle is 6° and said crest taper angle is 11°.

8. The screw according to claim 5, wherein said screw thread includes buttress means on a side of said screw thread remote from said back end so that forces applied to said screw thread from said back end axially toward said front end will be buttressed by said buttress means.

9. The screw according to claim 8, wherein said root taper angle is 6° and said crest taper angle is 11.4°.

10. The screw according to claim 1, wherein said body is constructed of a biocompatible material selected from the group consisting of a metal, a non-absorbable polymer, a ceramic and a bio-absorbable material.

11. The screw according to claim 10, wherein said biocompatible material is coated with a bio-absorbable coating having a low coefficient of friction.

12. The screw according to claim 11, wherein said coating includes one or more compounds selected from the group consisting of pharmaceuticals and bone growth factors.

13. An orthopedic interference screw for compression anchoring a bone graft in a bore formed in a bone mass, said screw comprising:

a biocompatible body with a root having front and back ends and further including an outer surface with a uniform taper at a root taper angle to a longitudinal axis of said screw between said front and back ends;

a screw thread formed over substantially all of said root, said screw thread including a crest with a uniform surface area along a length thereof and uniformly spirally expanding from said outer surface of said root from said front end to said back end so that an aggregate of said crests form a crest taper angle greater than said root taper angle;

wherein said screw thread includes buttress means on a side of said screw thread remote from said front end so that forces applied to said screw thread from said front end axially toward said back end will be buttressed by said buttress means; and wherein said root taper angle is in the range of 4° to 26° and said crest taper angle is in the range of 8° to 26°.

14. The screw according to claim 13, wherein said root taper angle is 6° and said crest taper angle is 11.4°.

15. The screw according to claim 13, wherein said screw is cannulated.

16. An orthopedic interference screw for compression anchoring a bone graft in a bore formed in a bone mass, said screw comprising:

a biocompatible body with a root having front and back ends and further including an outer surface with a uniform taper at a root taper angle to a longitudinal axis of said screw between said front and back ends; a screw thread formed over substantially all of said root, said screw thread including a crest with a uniform surface area along a length thereof and uniformly spirally expanding from said outer surface of said root from said front end to said back end so that an aggregate of said crests form a crest taper angle greater than said root taper angle;

wherein said screw thread includes buttress means on a side of said screw thread remote from said back end so that forces applied to said screw thread from said back end axially toward said front end will be buttressed by said buttress means; and wherein said root taper angle is in the range of 4° to 26° and said crest taper angle is in the range of 8° to 26°.

17. The screw according to claim 16, wherein said root taper angle is 6° and said crest taper angle is 11.4°.

18. The screw according to claim 16, wherein said screw is cannulated.

* * * * *